(12) United States Patent
Niiyama et al.

(10) Patent No.: US 9,823,173 B2
(45) Date of Patent: Nov. 21, 2017

(54) BLOOD MEASURING APPARATUS

(71) Applicant: NIHON KOHDEN CORPORATION, Tokyo (JP)

(72) Inventors: Yoshihiro Niiyama, Tokyo (JP); Satoshi Suzuki, Tokyo (JP); Koji Masuda, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 329 days.

(21) Appl. No.: 14/336,587

(22) Filed: Jul. 21, 2014

(65) Prior Publication Data
US 2015/0020613 A1  Jan. 22, 2015

(30) Foreign Application Priority Data

Jul. 22, 2013 (JP) .................................. 2013-151648

(51) Int. Cl.
*G01N 1/22* (2006.01)
*G01N 1/28* (2006.01)
(Continued)

(52) U.S. Cl.
CPC .............. *G01N 1/28* (2013.01); *G01N 15/12* (2013.01); *G01N 15/1404* (2013.01);
(Continued)

(58) Field of Classification Search
CPC .... G01N 15/12; G01N 33/49; G01N 15/1218; G01N 1/28; A61B 5/1468; A61L 2202/17
(Continued)

(56) References Cited

U.S. PATENT DOCUMENTS 5,728,351 A 3/1998 Carver, Jr.
6,259,242 B1 7/2001 Graham et al.
(Continued)

FOREIGN PATENT DOCUMENTS

EP 0 121 261 A2 10/1984
EP 2 463 655 A2 6/2012
(Continued)

OTHER PUBLICATIONS

The extended European Search Report for the related European Patent Application No. 14177978.5 dated Nov. 21, 2014.
(Continued)

*Primary Examiner* — Eric S McCall
*Assistant Examiner* — Mohammed E Keramet-Amircola
(74) *Attorney, Agent, or Firm* — Pearne & Gordon LLP

(57) ABSTRACT

A blood measuring apparatus includes: a liquid supply source storing a sheath liquid and applying a pressure to supply the sheath liquid to first and second chambers, pressures of the sheath liquids to be supplied to the first and second chambers different from each other; a sheath flow generator sending a blood sample supplied to the first chamber, to the aperture while causing the blood sample to be converged by a sheath flow due to the sheath liquid supplied from the liquid supply source; and a swirling flow generator causing the blood sample in the second chamber, to be converged by a swirling flow due to the sheath liquid supplied from the liquid supply source, thereby allowing the blood sample to flow in a direction separating from the aperture.

2 Claims, 1 Drawing Sheet

(51) Int. Cl.
*G01N 33/49* (2006.01)
*G01N 15/10* (2006.01)
*G01N 15/12* (2006.01)
*G01N 15/14* (2006.01)

(52) U.S. Cl.
CPC ..... *G01N 33/49* (2013.01); *G01N 2015/1006* (2013.01); *G01N 2015/1236* (2013.01); *G01N 2015/1263* (2013.01); *G01N 2015/1411* (2013.01)

(58) Field of Classification Search
USPC ....................................................... 73/863.21
See application file for complete search history.

(56) References Cited

U.S. PATENT DOCUMENTS

| | | | | |
|---|---|---|---|---|
| 2008/0122423 | A1* | 5/2008 | Luo | G01N 15/1209 324/71.4 |
| 2012/0146619 | A1* | 6/2012 | Niiyama | G01N 15/12 324/71.1 |
| 2015/0268221 | A1* | 9/2015 | Fukuda | G01N 33/48792 73/61.43 |

FOREIGN PATENT DOCUMENTS

| | | |
|---|---|---|
| JP | 59-184841 A | 10/1984 |
| JP | S60-128327 A | 7/1985 |
| JP | H08-075632 A | 3/1996 |
| JP | 2001-264233 A | 9/2001 |
| JP | 2003-501621 A | 1/2003 |
| JP | 2012-098203 A | 5/2012 |
| JP | 2012-127680 A | 7/2012 |

OTHER PUBLICATIONS

Japanese Office Action issued in Patent Application No. 2013-151648 dated Feb. 7, 2017.

\* cited by examiner

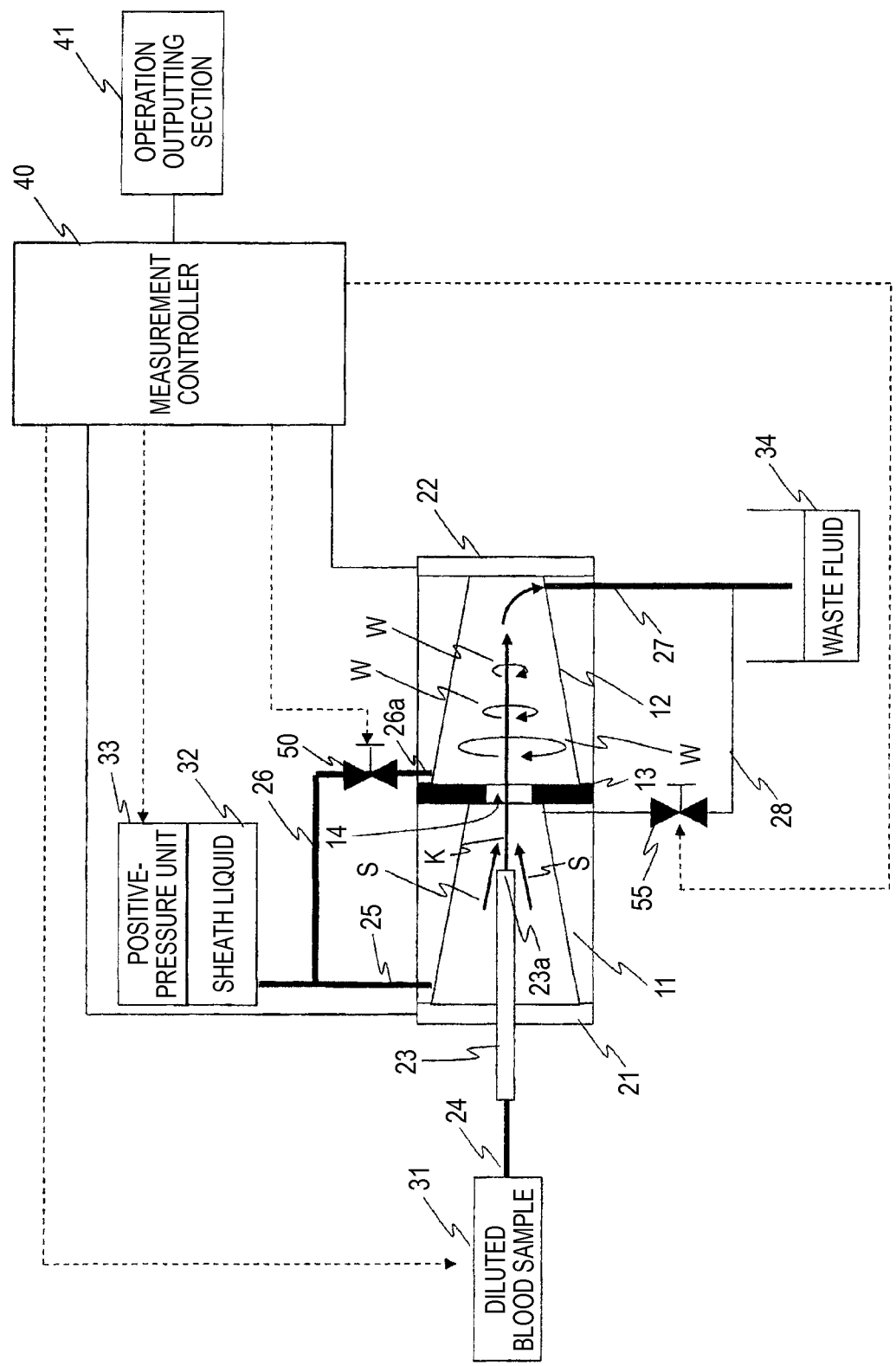

BLOOD MEASURING APPARATUS

CROSS-REFERENCE TO RELATED APPLICATION(S)

This application is based upon and claims the benefit of priority from prior Japanese patent application No. 2013-151648, filed on Jul. 22, 2013, the entire contents of which are incorporated herein by reference.

BACKGROUND

The presently disclosed subject matter relates to a blood measuring apparatus which performs a blood measurement by employing the electric resistance method.

JP-A-59-184841 discloses a configuration where, in order to correctly measure blood cells by employing the electric resistance method, a blood sample is caused to flow through the center of an aperture (sensing hole) by using a sheath flow on the upstream side of the aperture, thereby obtaining clean blood cell pulses. Also in such a configuration where a sheath flow is used upstream of an aperture, however, recirculation of blood cells occurs downstream of the aperture, and there arises a problem in that a measurement error is caused.

On the other hand, JP-A-2001-264233 and JP-T-2003-501621 disclose apparatuses having a configuration where, in the downstream side of an aperture, large blood cells which impede measurement of platelets are blocked from recirculating to the aperture, by using a back sheath or a sweep sheath. In measurement by such an apparatus, blood cells which have passed through the aperture do not recirculated to the sensing region in the aperture, and therefore a measurement error can be prevented from occurring.

In the configuration of a back sheath or a sweep sheath, however, blood cells are recovered before the jet flow defuses. Therefore, a mechanism for this purpose must be attached to the vicinity of the aperture, and hence the configuration is complicated. In the configuration, moreover, a sheath liquid is flown through a recovery pipe. Consequently, the flow is weak in the vicinity of the aperture, and therefore it is difficult to remove floating blood cells, bubbles adhering to, for example, a partition wall in which the aperture is formed.

To comply with the above, the applicant has proposed in JP-A-2012-127680 a blood measuring apparatus in which a swirling flow is generated by sucking a diluting solution on the downstream side of an aperture to block blood cells from recirculating to a sensing region, whereby measurement is prevented from being erroneously performed.

The blood measuring apparatus provided by the applicant achieves the very excellent effects as described above. The presently disclosed subject matter has been conducted in order to provide a further improved blood measuring apparatus.

SUMMARY

The presently disclosed subject matter may provide a blood measuring apparatus in which blood cells can be prevented from being recirculated to a sensing region, and the accuracy of measurement of blood cells can be further improved.

The blood measuring apparatus may comprise: first and second chambers which communicate with each other through an aperture; first and second electrodes which are provided with the first and second chambers, respectively; a liquid supply source which is configured to store a sheath liquid, and which is configured to apply a pressure to supply the sheath liquid to the first and second chambers, a pressure of the sheath liquid to be supplied to the first chamber different from a pressure of the sheath liquid to be supplied to the second chamber; a sheath flow generator which is configured to send a blood sample supplied to the first chamber, to the aperture while causing the blood sample to be converged by a sheath flow due to the sheath liquid supplied from the liquid supply source; and a swirling flow generator which is configured to cause the blood sample in the second chamber, to be converged by a swirling flow due to the sheath liquid supplied from the liquid supply source, thereby allowing the blood sample to flow in a direction separating from the aperture.

The liquid supply source may include: a single liquid supply source which is configured to supply the sheath liquid to the first and second chambers; a first supply path through which the sheath liquid is supplied to the first chamber; and a second supply path through which the sheath liquid is supplied to the second chamber.

The blood measuring apparatus may further comprise: a flow controller which is disposed in the second supply path, and which is configured to adjust a flow rate in the second supply path.

The flow controller may include a valve.

The flow controller may be configured by changing at least one of a length and a diameter of the path.

The liquid supply source may include: a first liquid supply source which is configured to supply the sheath liquid to the first chamber; and a second liquid supply source which is configured to supply the sheath liquid to the second chamber.

A pressure for supplying the sheath liquid from the second liquid supply source to the second chamber may be lower than a pressure for supplying the sheath liquid from the first liquid supply source to the first chamber.

BRIEF DESCRIPTION OF THE DRAWINGS

FIG. 1 is a diagram of a blood measuring apparatus of an embodiment of the presently disclosed subject matter.

DETAILED DESCRIPTION OF EXEMPLARY EMBODIMENTS

Hereinafter, a blood measuring apparatus of an embodiment of the presently disclosed subject matter will be described with reference to the accompanying drawing. FIG. 1 is a diagram of the blood measuring apparatus of the embodiment of the presently disclosed subject matter. The blood measuring apparatus may include a first chamber 11 and a second chamber 12. The first chamber 11 and the second chamber 12 communicate with each other through an aperture 14 which is a sensing region formed in a middle portion of a partition wall 13 that separates the first and second chambers from each other.

A first electrode 21 is disposed on a surface of the first chamber 11 opposed to the aperture 14. The first chamber 11 maybe configured by a chamber having, for example, a truncated conical shape in which the diameter is smaller in a tapered manner with progressing from the first electrode 21 toward the aperture 14. A second electrode 22 is disposed on a surface of the second chamber 12 opposed to the aperture 14. The second chamber 12 may be configured by a chamber having, for example, a truncated conical shape in which the diameter is smaller in a tapered manner with progressing from the partition wall 13 toward the second electrode 22.

A sample supply pipe 23 is coupled with the first chamber 11. The sample supply pipe 23 is disposed so as to extend from the outside of the first chamber 11 into the first chamber 11 through the middle of the first electrode 21. A diluted blood sample is supplied from a sample supplying section 31 to the sample supply pipe 23 through a tube 24.

The first chamber 11 is connected to a sheath liquid reservoir 32 through a tube (first supply path) 25, and the second chamber 12 is connected to the sheath liquid reservoir 32 through a tube (second supply path) 26. A sheath liquid which functions as a diluting solution is stored in the sheath liquid reservoir 32. The sheath liquid reservoir 32 is provided with a positive-pressure unit 33 which pressurizes the sheath liquid. Based on a control of a measurement controller 40, the positive-pressure unit 33 applies a positive pressure to the sheath liquid in the sheath liquid reservoir 32 to send out the sheath liquid. As described above, the blood measuring apparatus of the embodiment includes the liquid supply source which applies a positive pressure to supply the sheath liquid to the first chamber 11 and the second chamber 12.

The tip end of the tube 25 is connected to the first chamber 11 and the vicinity of the first electrode 21. A sample supply port 23a which is the tip end of the sample supply pipe 23 is disposed closer to the aperture 14 than the tip end of the tube 25. According to the configuration, the sheath liquid supplied through the tube 25 generates a sheath flow S directed toward the aperture 14, so as to surround a sample flow K of the diluted blood sample discharged from the sample supply pipe 23. As described above, the blood measuring apparatus includes a sheath flow generator which sends the blood sample supplied to the first chamber 11, to the aperture 14 while causing the blood sample to be converged by the sheath flow S.

A flow controller 50 which adjusts the flow rate of the liquid discharged from the second chamber 12, to a predetermined value is disposed at the vicinity of the tip end 26a of the tube 26 which is adjacent to the partition wall 13 in the second chamber 12. The flow controller 50 operates so as to differentiate the pressure of the sheath liquid supplied to the first chamber 11 through the tube 25, from that of the sheath liquid supplied to the second chamber 12 through the tube 26, and adjusts the flow rate of the sheath liquid supplied to the second chamber 12 through the tube 26, to a predetermined value.

The flow controller 50 may be configured by a valve. When the degree of opening of a valve which functions as the flow controller 50 is controlled to perform a flow rate adjustment (pressure adjustment), the pressure difference between the first chamber 11 which is upstream of the aperture 14, and the second chamber 12 which is downstream of the aperture 14 is set to a desired value. Namely, the pressure in the first chamber 11 is made higher than that in the second chamber 12, to allow the sheath flow S passing through the aperture 14 to flow toward the second electrode 22 in a state where the sheath flow surrounds the sample flow K of the diluted blood sample in a sheath-like manner. When the degree of opening of the valve is controlled to adjust the flow rate, the sample flow K in a swirling flow W can have a desired squeezed diameter. Of course, it is also possible that the degree of opening of the valve is desirably controlled to adjust the flow rate, the flow rate of the sample flow K of the diluted blood sample is adjusted, and the sample flow K in the swirling flow W is caused to have a desired squeezed diameter. In any case, the speed (intensity) at which the sheath flow S in the state where the sheath flow surrounds the sample flow K of the diluted blood sample proceeds in the swirling flow W can be desirably adjusted in an easy manner.

The flow controller 50 is not limited to the valve, and maybe configured by changing the length and/or diameter of the means constituting the path, such as a tube.

A waste fluid tube 27 is connected to an end portion on the side of the second electrode 22. The fluid in the second chamber 12 is discharged to a waste fluid reservoir 34 through the waste fluid tube 27. Because of this configuration and the above-described flow rate adjustment (pressure adjustment) by the flow controller 50, the sheath liquid discharged from the tip end 26a of the tube 26 flows along the inner wall of the second chamber 12 which is in proximity to the peripheral edge of the partition wall 13, and the swirling flow W is generated which swirlingly flows so as to wind around the sheath flow S flowing at a high flow rate over the whole second chamber 12. The swirling flow W swirls about the sample flow K of the diluted blood sample which proceeds from the aperture 14 into the second chamber 12, and advances toward the waste fluid tube 27. Moreover, the sheath flow S advances toward the waste fluid tube 27 in the state where the sheath flow surrounds the sample flow K of the diluted blood sample. As described above, the blood measuring apparatus is provided with a swirling flow generator which causes the blood sample that flows from the aperture 14 to the second chamber 12, to be converged by the swirling flow W due to the sheath liquid supplied from the liquid supply source, thereby allowing the blood sample to flow in the direction separating from the aperture 14.

Furthermore, the tip end 26a of the tube 26 which is ahead of the flow controller 50 is connected to the second chamber 12 and the vicinity of the partition wall 13. In the connection portion, as described in JP-A-2012-127680 of the earlier patent application filed by the applicant of the present application, for example, the tip end 26a of the tube 26 may be disposed so that the sheath liquid discharged from the tip end 26a of the tube 26 is directed to flow along the inner wall of the second chamber 12 adjacent to the peripheral edge of the partition wall 13. This configuration functions so as to adequately assist the generation of the swirling flow W which whirls along the inner wall of the partition wall 13 on the side of the second chamber 12, and which flows toward the second electrode 22. The momentum of the swirling flow is maintained by forming the chamber 12 into a tapered shape or gradually reducing the diameter.

The first electrode 21 and the second electrode 22 are connected to the measurement controller 40. The measurement controller 40 is connected to an operation outputting section 41 having an outputting portion which displays or prints characters and the like, and an operating portion in which keys are disposed. The measurement controller 40 controls the opening and shutting of a valve 55 disposed in a tube 28 connecting the first chamber 11 with the waste fluid reservoir 34. In order to perform the measurement, specifically, the valve 55 is shut to fill the first chamber 11 with the sheath liquid, and the discharge of the liquid from the second electrode 22 is stopped by controlling a flow path opening/closing unit which is disposed in the waste fluid tube 27 and which is not shown, to fill the second chamber 12 with the sheath liquid. During the measurement, the valve 55 is continued to be shut, and the flow path opening/closing unit which is not shown is controlled so as to enable the discharge of the liquid from the second chamber 12. Moreover, the sample supplying section 31 is controlled to supply the diluted blood sample to the first chamber 11. Furthermore, the measurement controller 40 functions as a measuring unit which causes a minute current to flow between the first and second electrodes 21, 22 to perform a blood measurement.

The measurement controller 40 captures a change of the electric resistance due to blood cells in the sample flow K which flows from the first chamber 11 to the second chamber 12 through the aperture 14, and which exists between the first and second electrodes 21, 22, and performs a blood cell counting based on the change. A result of the measurement is output from the operation outputting section 41.

During the measurement, moreover, the measurement controller 40 controls the positive-pressure unit 33 so as to supply the sheath liquid from the sheath liquid reservoir 32 to the first and second chambers 11, 12. At this time, the flow controller 50 sets the state where the intensities of the sheath flow S and the swirling flow W are adjusted to respective desired values as described above.

Therefore, the sheath flow S of the desired intensity is produced in the first chamber 11, and the swirling flow W of the desired intensity is generated in the second chamber 12. A new sheath liquid which causes the swirling flow W to be generated flows to the vicinity of the aperture 14, and bubbles and blood do not adhere to the vicinity of the aperture 14, thereby enabling the measurement to be accurately performed. Together with this, the swirling flow W prevents the jet flow of the diluted blood sample from diffusing, and enables the measurement to be accurately performed without causing the diluted blood sample to be recirculated to the sensing region such as the vicinity of the aperture 14. When the flow rate of the sample flow K is changed with respect to the above-described adjusted flow, the squeezed diameter of the sample flow K passing through the aperture 14 can be set to a desired value. According to the configuration, it is also possible that a diluted blood sample having a small number of blood cells is supplied (flown) in a large amount to increase the passage amount of blood cells, and therefore the accuracy of measurement of blood cells can be improved.

Although, in the above, the configuration has been described where the single liquid supply source supplies the sheath liquid to the first and second chambers 11, 12, the liquid supply source is not limited to this . Alternatively, the liquid supply source may have a configuration where the source includes a first liquid supply source which supplies the sheath liquid to the first chamber 11, and a second liquid supply source which supplies the sheath liquid to the second chamber 12, and the pressures of the sheath liquids to be supplied respectively to the first and second chambers 11, 12 are different from each other. Preferably, the pressure of the second liquid supply source is lower than that of the first liquid supply source. Also in the alternative, it is possible to achieve similar effects as those of the embodiment.

The blood measuring apparatus of the presently disclosed subject matter includes: the sheath flow producing unit which is configured to send the blood sample supplied to the first chamber, to the aperture while causing the blood sample to be converged by the sheath flow due to the sheath liquid supplied from the liquid supply source; and the swirling flow producing unit which is configured to cause the blood sample that flows from the aperture to the second chamber, to be converged by the swirling flow due to the sheath liquid supplied from the liquid supply source, thereby allowing the blood sample to flow in the direction separating from the aperture. The pressures of the sheath liquids to be supplied respectively to the first and second chambers are different from each other. In front of the aperture, therefore, the sample can be sent toward the aperture while being converged by the sheath flow, and, in rear of the aperture, the sample can flow while being converged by the swirling flow, without causing recirculation. Consequently, measurement can be prevented from being erroneously performed.

In the blood measuring apparatus of the presently disclosed subject matter, a swirling flow is generated in rear of the aperture by the simple configuration where the pressures of the sheath liquids to be supplied respectively to the first and second chambers are different from each other, thereby allowing the sample to be converged and flow without causing recirculation. Therefore, measurement can be prevented from being erroneously performed.

What is claimed is:

1. A blood measuring apparatus comprising:
   first and second chambers which communicate with each other through an aperture;
   first and second electrodes which are provided with the first and second chambers, respectively;
   a liquid supply source which is configured to store a sheath liquid, and which is configured to apply a pressure to supply the sheath liquid to the first and second chambers, a pressure of the sheath liquid to be supplied to the first chamber different from a pressure of the sheath liquid to be supplied to the second chamber;
   a sheath flow generator which is configured to send a blood sample supplied to the first chamber, to the aperture while causing the blood sample to be converged by a sheath flow due to the sheath liquid supplied from the liquid supply source; and
   a swirling flow generator which is configured to cause the blood sample in the second chamber, to be converged by a swirling flow due to the sheath liquid supplied from the liquid supply source, thereby allowing the blood sample to flow in a direction separating from the aperture;
   wherein the liquid supply source includes:
      a single liquid supply source which is configured to supply the sheath liquid to the first and second chambers;
      a first supply path through which the sheath liquid is supplied to the first chamber; and
      a second supply path through which the sheath liquid is supplied to the second chamber,
   wherein the blood measuring apparatus further comprises a flow controller which is disposed in the second supply path, which is configured to adjust a flow rate in the second supply path, and which is configured by changing at least one of a length and a diameter of the second supply path.

2. The blood measuring apparatus according to claim 1, wherein the flow controller includes a valve.

* * * * *

UNITED STATES PATENT AND TRADEMARK OFFICE
CERTIFICATE OF CORRECTION

PATENT NO. : 9,823,173 B2  
APPLICATION NO. : 14/336587  
DATED : November 21, 2017  
INVENTOR(S) : Yoshihiro Niiyama et al.

Page 1 of 1

It is certified that error appears in the above-identified patent and that said Letters Patent is hereby corrected as shown below:

In the Specification

Column 4, Line 7, "maybe" should read --may be--

Signed and Sealed this
Twenty-seventh Day of March, 2018

Andrei Iancu
*Director of the United States Patent and Trademark Office*